US009518914B2

(12) United States Patent
Gurkan et al.

(10) Patent No.: US 9,518,914 B2
(45) Date of Patent: Dec. 13, 2016

(54) PORTAL AND METHOD FOR MANAGEMENT OF DIALYSIS THERAPY

(71) Applicants: Umut A. Gurkan, Cambridge, MA (US); Utkan Demirci, Cambridge, MA (US); Derya A. Yellin, Cambridge, MA (US)

(72) Inventors: Umut A. Gurkan, Cambridge, MA (US); Utkan Demirci, Cambridge, MA (US); Derya A. Yellin, Cambridge, MA (US)

(73) Assignee: BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 14/430,360

(22) PCT Filed: Mar. 24, 2013

(86) PCT No.: PCT/US2013/061292
§ 371 (c)(1),
(2) Date: Mar. 23, 2015

(87) PCT Pub. No.: WO2014/047608
PCT Pub. Date: Mar. 27, 2014

(65) Prior Publication Data
US 2015/0219545 A1    Aug. 6, 2015

Related U.S. Application Data

(60) Provisional application No. 61/704,692, filed on Sep. 24, 2012.

(51) Int. Cl.
*G06K 9/00* (2006.01)
*G01N 15/10* (2006.01)
(Continued)

(52) U.S. Cl.
CPC ..... *G01N 15/1056* (2013.01); *B01L 3/502761* (2013.01); *G01N 15/1436* (2013.01);
(Continued)

(58) Field of Classification Search
CPC .............. G06F 19/345; G06K 9/00127; G01N 2015/1006; G01N 15/1484; G01N 15/1475; G01N 15/1463
See application file for complete search history.

(56) References Cited

U.S. PATENT DOCUMENTS

2002/0186875 A1* 12/2002 Burmer ................ G06K 9/66
382/133
2006/0257013 A1* 11/2006 Ramm ............... G01N 15/1475
382/133
(Continued)

OTHER PUBLICATIONS

International Search Report under date of mailing of Feb. 6, 2014 in connection with PCT/US2013/061292.

*Primary Examiner* — Bhavesh Mehta
*Assistant Examiner* — Ian Lemieux
(74) *Attorney, Agent, or Firm* — Yakov Sidorin; Quarles & Brady LLP

(57) ABSTRACT

System and method for point-of-care monitoring of neutrophils in a peritoneal dialysis sample with the use of a microfluidic system. The immunoassay based chip is configured to bound neutrophils to a microfluidic channel surface while leaving auxiliary cells and particles unattached and suspended in the sample and flushable with a wash buffer. Data representing images of neutrophils, formed by an (optionally lensless) imaging system, are processed to determine a count of neutrophils based on statistical parameters including characteristics of the microfluidic channel.

11 Claims, 12 Drawing Sheets

(51) Int. Cl.
  *G01N 33/543* (2006.01)
  *G01N 15/14* (2006.01)
  *B01L 3/00* (2006.01)
  *G06F 19/00* (2011.01)
  *G01N 15/00* (2006.01)

(52) U.S. Cl.
  CPC ... *G01N 15/1484* (2013.01); *G01N 33/54366* (2013.01); *G06F 19/345* (2013.01); *G06K 9/00127* (2013.01); *B01L 2300/023* (2013.01); *B01L 2300/027* (2013.01); *B01L 2300/0654* (2013.01); *B01L 2300/0816* (2013.01); *G01N 2015/008* (2013.01); *G01N 2015/1006* (2013.01); *G01N 2015/1062* (2013.01)

(56) References Cited

U.S. PATENT DOCUMENTS

| | | | |
|---|---|---|---|
| 2008/0317325 A1* | 12/2008 | Ortyn | G01N 15/147 382/133 |
| 2009/0053204 A1* | 2/2009 | Denlinger | G01N 33/5094 424/130.1 |
| 2009/0215072 A1* | 8/2009 | McDevitt | G01N 21/6428 435/7.1 |
| 2011/0151498 A1 | 6/2011 | Quake et al. | |
| 2011/0312067 A1* | 12/2011 | Silverbrook | B01L 3/5027 435/283.1 |
| 2011/0312549 A1 | 12/2011 | Azimi et al. | |
| 2012/0063664 A1* | 3/2012 | Di Carlo | G01N 15/1404 382/133 |
| 2012/0218379 A1* | 8/2012 | Ozcan | G01N 15/1475 348/40 |
| 2016/0139035 A1* | 5/2016 | Florescu | B01L 3/502761 506/40 |

* cited by examiner

PORTAL AND METHOD FOR MANAGEMENT OF DIALYSIS THERAPY

CROSS-REFERENCE TO RELATED APPLICATIONS

This application represents the national stage entry of PCT International Application No. PCT/US2013/061292 filed Sep. 24, 2013, which claims the benefit of U.S. Provisional Patent Application Ser. No. 61/704,692 filed Sep. 24, 2012. The disclosures of both of the above-mentioned applications are incorporated herein by reference for all purposes.

STATEMENT REGARDING FEDERALLY SPONSORED RESEARCH OR DEVELOPMENT

This invention was made with government support under Grants Numbers R01 AI081534, W81XWH-10-1-1050, and R21 AI087107. The government has certain rights in the invention.

TECHNICAL FIELD

The present invention relates to system and method adapted to expedite a determination of the required treatment based on a point-of-care measurement of a bodily fluid sample.

BACKGROUND

A large portion—in excess of 8 percent in 2009—of funds available under the Medicare program is directed towards the treatment and medications of End Stage Renal Disease (ESRD) patients, which emphasizes the significance of this area of medical treatment. The success of the sought treatments, however, remains substantially low as evidenced by the related statistical data. According to 1999-2004 National Health and. Nutrition Examination Survey (NHANES), the prevalence of chronic kidney disease (CKD) in the US adult population was about 16.8% of the overall U.S. population 20 years and older, which indicated a significant increase as compared to the numbers determined in 1988, for example. For CKD patients with ESRD, kidney replacement or dialysis to preserve any residual renal function is commonly required. Millions of people worldwide are receiving renal replacement therapy, and this number grows at an annual rate of about 8%. Treatments for the ESRD account for $39.5 billion US dollars in both public and private spending.

The examination of bodily fluid samples provides support for patient care to-date. For example, hemodialysis (HD) and peritoneal dialysis (PD) are the currently employed methods to treat advanced and permanent kidney failure. The PD patients account for about 7% of all dialysis patients in the USA as compared to outside the US (Canada, Mexico, Europe, Asia) where this number is much higher (between 35% and 80%). The PD treatment is recognized to be significantly less expensive than the HD treatment per year per patient. Incentives are emerging to keep patients on PD therapy. For example, a patient may qualify immediately for the PD coverage, whereas the HD coverage does not begin until after a 90 day grace period. Accordingly, the HD may be considered inconvenient by many patients, who would find it hard to travel to a HD center several times per week and spend between 3 and 5 hours per visit on an HD procedure that requires support from a healthcare team. Nevertheless, both the HD and PD procedures re found to be quite useful.

Home-based therapy, which includes home hemodialysis and PD, would provide an advantageous alternative to the existing implementations of the HD and PD due to lower cost and higher patient satisfaction. Barriers to home-based implementation of PD are defined, in part, by the risk of recurring peritonitis or inflammation of the peritoneum that diminishes the filtering properties of the peritoneal membrane and potentially reduces the time-window available for kidney transplant. Peritonitis is clinically defined as the occurrence of a turbid effluent in the dialysate containing more than 100 white blood cells (WBCs) per microliter, of which more than 50% are neutrophils The PD patients exchange the PD fluid 2-5 times a day. When the PD procedures are implemented as home-based procedures, patients are expected to observe the cloudiness/turbidity of their dialysate at every exchange and initiate a call to their caregivers if they observe cloudiness in the fluid. However, interpretations based on cloudiness of the dialysate do not provide the accurate means to predict peritonitis Accordingly, there exists a need in a practical modality overcoming the above-described deficiencies.

SUMMARY

Embodiments of the present invention provide a system for at least one of identifying and counting target cells in a bodily fluid sample, the system including an element with a network of microfluidic channels, a light source, an optical detector positioned adjacently to the element without an optical component therebetween such that the optical detector is adapted to receive light through the element, and a non-transitory computer readable medium having computer readable program code for counting target cells in a fluid dialysis sample. The dialysis sample may include but not limited to a hemodialysis or peritoneal dialysis sample. The program code includes a series of computer readable program steps to effect (i) acquiring data representing a gray-scale image (or color image, or multi- or hyperspectral image) of said network formed on a surface of the optical detector in light that has traversed the network of microfluidic channels; and (ii) processing the acquired data to obtain a visually-enhanced image using state-of-the-art techniques of image enhancement to standardize the input image, as well as effectuating a feature detection to identify structural features of the carrier in which the dialysis sample is contains, and using shape detection and morphology identification algorithm to perform cell identification and count in the dialysis sample. In one example, the processing of data may include (iia) converting the acquired data to data representing a gray-scale image of the network of channels; (iib) at least one of filtering in a frequency domain and filtering in a spatial domain of so converted data; and (iic) when a channel of the network contains a fluidic sample with identified biological cells, counting the cells in relation to the channel parameters and a predefined threshold value to determine a count value.

Embodiments of the invention also provide a system for at least one of identifying and counting target cells in a bodily fluid sample, which system includes a plurality of microfluidic channels; a light source positioned to transmit light through this plurality of channels; an optical detector positioned adjacent to the plurality of channels to receive light from the light source after passing through the plurality of channels such as to form an irradiance distribution representing the sample contained in at least one of the plurality of channels at the optical detector; and one or more processors having thereon operational computer code configured to perform one or more steps of a method for at least one of identifying and counting target cells in the sample. Such method includes (i) acquiring data representing an initial image of the plurality of channels formed on a surface of the optical detector in light that has traversed the channels; (ii) converting the acquired data to monochrome image data representing the plurality of microfluidic channels; and (iii) processing the monochrome image data by filtering the data in at least one of a frequency domain and a spatial domain. The method may further include a step of identifying target cells from the processed monochrome image data and, optionally, counting the identified target cells.

Embodiments of the invention additionally provide an article of manufacture comprising a microprocessor and a computer readable medium that includes computer readable program code for counting target cells in a fluid peritoneal dialysis sample contained in a channel of a microfluidic system. The system includes a microfluidic chip having one or more of channels; an optical detector adjacent to the microfluidic chip; and a light source adapted to transmit light through the channel onto the optical detector such as to form an image in the fluid peritoneal dialysis sample at the detector in absence on an imaging optical component. The computer readable program code includes a series of program steps to enable counting of the target cells based at least in part on conversion of data representing the formed image from color scale to gray scale. Additionally or alternatively, the computer readable program code further comprises steps to enable the counting of cells based on a probability of the target cells to be located near a surface of the channels and a likelihood of bond formation between so located cells and receptors.

Embodiments of the invention additionally provide a system for at least one of identifying and counting target cells in a bodily fluid sample. The system includes one or more computer processors and a computer-readable medium comprising computer code which is configured to perform, when used to operate one or more computer processors, one or more steps of a method for at least one of identifying and counting target cells in a bodily fluid sample. The system includes a microfluidic chip having one or more microfluidic channels; an optical detector adjacent to the microfluidic chip; and a light source adapted to transmit light through a microfluidic channels onto the optical detector such as to form an irradiance distribution representing the bodily fluid sample at the optical detector in absence of an optical component forming an optical conjugate of the fluid sample at the detector. In such a system, the step(s) of the method are effectuated based at least in part on conversion of data representing the formed irradiance distribution to a monochrome scale.

Embodiments additionally provide a method for identifying cells contained in a fluid peritoneal dialysis sample. Such method includes (i) receiving data representing an image of neutrophils formed in light, that has traversed a microfluidic channel containing said fluid sample, without the use of an optical imaging component; and (ii) processing the received data to determine a count of the neutrophils based on probability of the cells to be located near a surface of the microfluidic channel and likelihood of bond formation between so located cells and receptors. The method may further include determining a probability of a steady-state adhesion of the neutrophils to the surface of the microfluidic channel. Alternatively or in addition, the method may include generating visually-perceivable triggering indicator when the determined count exceeds a threshold value adjustable based on a user input.

Embodiments additionally provide a method for at least one of identifying and counting target cells in a bodily fluid sample, which method includes (i) providing a system comprising a plurality of microfluidic channels, a light source configured to transmit light through such plurality of channels, and an optical detector configured to receive light from the light source after passing through the plurality of channels such as to form an irradiance distribution representing the fluid sample at the detector; (ii) arranging the bodily fluid sample in at least one of the plurality of channels; (iii) illuminating the plurality of channels with the light source; (iv) acquiring data representing an initial image of the plurality of channels at the detector in transmission of light through at least one channel; (iv) converting the acquired data to monochrome image data; (v) processing the monochrome image data by filtering these data in at least one of a frequency domain and a spatial domain; (vi) identifying target cells from the processed monochrome image data; and optionally counting the identified target cells.

Embodiments additionally provide a non-transitory tangible computer readable medium having stored thereon computer code operational on one or more processors of a computer system to perform a method for at least one of identifying and for counting target cells contained in a bodily fluid sample, which method comprises acquiring data representing an initial image of at least one of a plurality of microfluidic samples on a surface of an optical detector in light from a light source that has passed through the at least one of the plurality of channels. The method additionally includes converting the acquired data to monochrome image data and processing the monochrome image data by filtering these data in at least one of a frequency domain and a spatial domain. The method further includes identifying target cells from the processed monochrome image data and, optionally, counting the identified target cells.

BRIEF DESCRIPTION OF THE DRAWINGS

The invention will be more fully understood by referring to the following Detailed Description in conjunction with the Drawings, of which.

DETAILED DESCRIPTION

Figure 1:
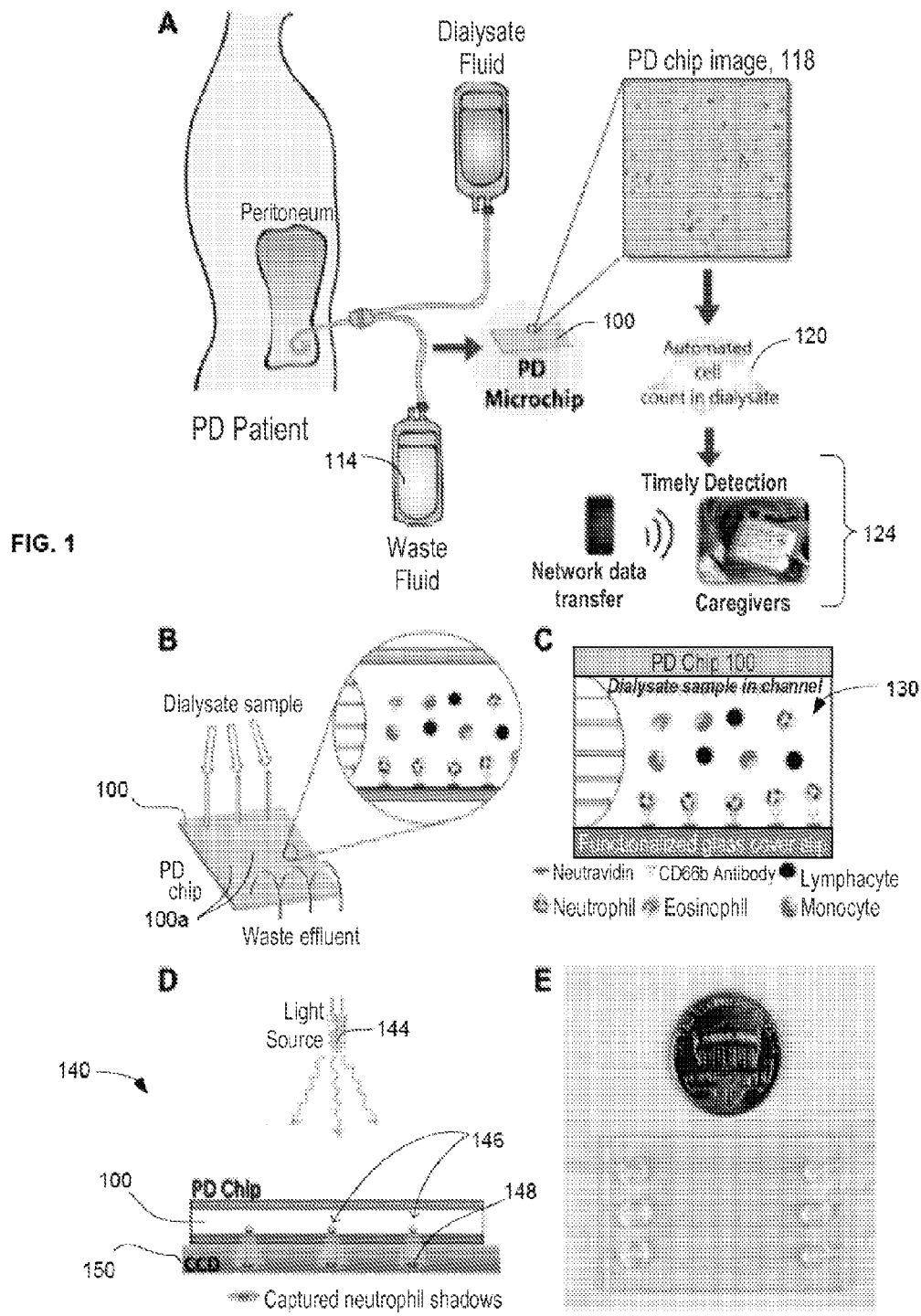
FIG. 1 provides diagrams A through E illustrating the infection monitoring in peritoneal dialysis (PD) patient with the use of a point-of-care embodiment of a microchip of the invention.

Hemodialysis (also referred to as haemodialysis, or HD) is a method that is used to achieve the extracorporeal removal of waste products such as creatinine and urea and free water from the blood when the kidneys are in a state of renal failure. Peritoneal dialysis is used as an alternative to HD, though it is far less commonly used. While the PD, as compared to traditional HD, provides higher quality of care, both procedures are available and provide ease of access to the patients. It is understood that, while in the disclosure below, the reference is made to PD, such reference is made only to make the disclosure concise and that the use of HD fluid or any other bodily fluid as a sample for analysis discussed below was considered to be within the scope of the invention.

A recognized clinical barrier in peritoneal dialysis is the risk of peritonitis, i.e. inflammation of peritoneum. Peritonitis is clinically defined as the occurrence of a turbid dialysate containing more than 100 white blood cells (WBCs) per microliter of which more than 50% are neutrophils. As infection progresses, a substantial increase in WBCs results in higher degree of opaqueness of the peritoneal dialysate. However, at the early stages of infection the change in the turbidity is not visually detectable.

The decision-making on whether the infection has occurred is currently based on assessment, by the patient himself, of a degree of opaqueness and visually perceived cloudiness of the bodily fluid such as the dialysate, which is understandably subjective and, at least for that reason, is not quite adequate to monitor peritonitis. Clinically, the WBCs and neutrophil counts are used to assess the occurrence of peritonitis. On the other hand, since a cell counting platform is not accessible at the point-of-care (POC), when the bodily fluid or dialysate appears turbid, it is considered to be an indication of a potential infection and patients are expected to initiate a call to their caregivers followed by an immediate visit to the doctor's office or emergency room. In reference to Table 1, the observations performed by patients can, overall, be misleading causing unnecessary emergency room visits, hospitalizations, and subsequent doctor office visits, which could have been avoided with reliable bedside testing.

TABLE 1

Results of comparison of the use of an embodiment with current clinical practice

|  | PD microchip | Current standard practice at home | Current standard practice at clinic |
| --- | --- | --- | --- |
| Clinical practice/method | Microchip | Visual turbidity measurement | Flow cytometer (FACS) |
| Reproducibility | Quantitative | Not quantitative | Quantitative |
| Accuracy | High | Low | High |
| Time | <1 hour | Depends on how long it takes the patient to decide | 1-2 days for results to come from the clinic (30 min. analysis time) |
| Cost | <1 USD per test | N/A | 50 USD per test |
| Trained personnel | No | No | Yes |
| Differential cell count | Yes | No quantitative data | Yes |
| Actionable outcome | Yes | Yes, if the patient | Yes |

The above-described situation is exacerbated by the facts that (i) the bodily fluid or dialysate's cloudiness (turbidity) can be caused by other reasons (for example, drugs such as manidipine hydrochloride, a dihydropyridine-type calcium channel blocker) that do not necessarily indicate peritonitis, and (ii) the lack of appropriate quantitative monitoring technology complicates the monitoring of the health status of a HD/PD patient. Overall, there exists a not addressed yet, unmet clinical need for rapid and quantitative monitoring of a dialysate to determine the risk of infection.

To address this clinical need, embodiments of the present invention provide a disposable bodily fluid microchip (for example, an HD/PD microchip) and a corresponding method for operation of such microchip to enable rapid quantification of neutrophils in a dialysate to monitor the health status of an HD/PD patient. In a pilot study, neutrophil microchip counts in dialysates of 20 HD/PD patients were obtained (ranging from 16±2 to 842±29 neutrophils per 100 microliters) over a time period of up to 190 days. An HD/PD microchip was operable to successfully determine the status of the patients. The proposed embodiments are broadly applicable for rapid quantitative analysis of body fluids at the bedside/point of care location, covering a broad range of diseases that require continuous or repetitive monitoring. References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole, including features disclosed in prior art to which reference is made.

As was already alluded to above, while in the examples discussed below, the references are made only to PD, such references are made only for the sake of keeping the description concise and simplified, and use of HD procedure and HD fluid sample or any other bodily fluid as a sample for analysis intended to be within the scope of the invention.

In reference to FIG. 1, diagrams A through E are used to illustrate the principle of monitoring the infection in PD patients using a point-of-care embodiment. A PD microchip 100 uses a small volume of waste dialysate 114 from the patient effluent to capture $CD66b^+$ neutrophils on a surface of a channel of the chip 100 with high specificity and efficiency. An image 118 of the microchip is taken and the captured neutrophils are quantified with automated software, 120. As shown at 124, the determined dialysate neutrophil counts are optionally sent to storage such as electronic records, for example, which can then be assessed by the caregivers to monitor the risk of infection during PD treatment. The diagram B illustrates the injection of PD patient dialysate samples into the channels 100a of the microchip 100 to selectively capture the neutrophils at the channel surface. The diagram C provides a schematic representation of a functionalized channel surface 130 with CD66 antibody and captured neutrophils from a pool of white blood cells in dialysate. While the $CD66^+$ neutrophils are selectively captured on the channel 100a, other cells flow and exit the channel without being captured, substantially unabated. The diagram D illustrates, schematically, a means for imaging, detection and quantification of the neutrophils captured in the channels 100a of the chip 100. The means 140 includes a light source 144 adapted to illuminate the chip 100 and the captured cells 146 such that the shadows 148 of the captured cells 146 are projected onto the surface of a charge coupled device (CCD) sensor 150. The means 140 is configured such that the CCD 150 is enabled to detect the light intensity distribution corresponding to the shadows 148 of the captured cells 146 without the need for an objective lens and with the use of an automated cell recognition and quantification computer program product loaded on a computer system. The diagram E presents, in the top view, an image of an embodiment of the PD microfluidic chip 100.

In the following portion of the present disclosure, in reference to FIGS. 2 through 8, non-limiting examples embodiments of a system and method for acquisition and processing of an image of neutrophils are discussed in more detail.

Figure 2:
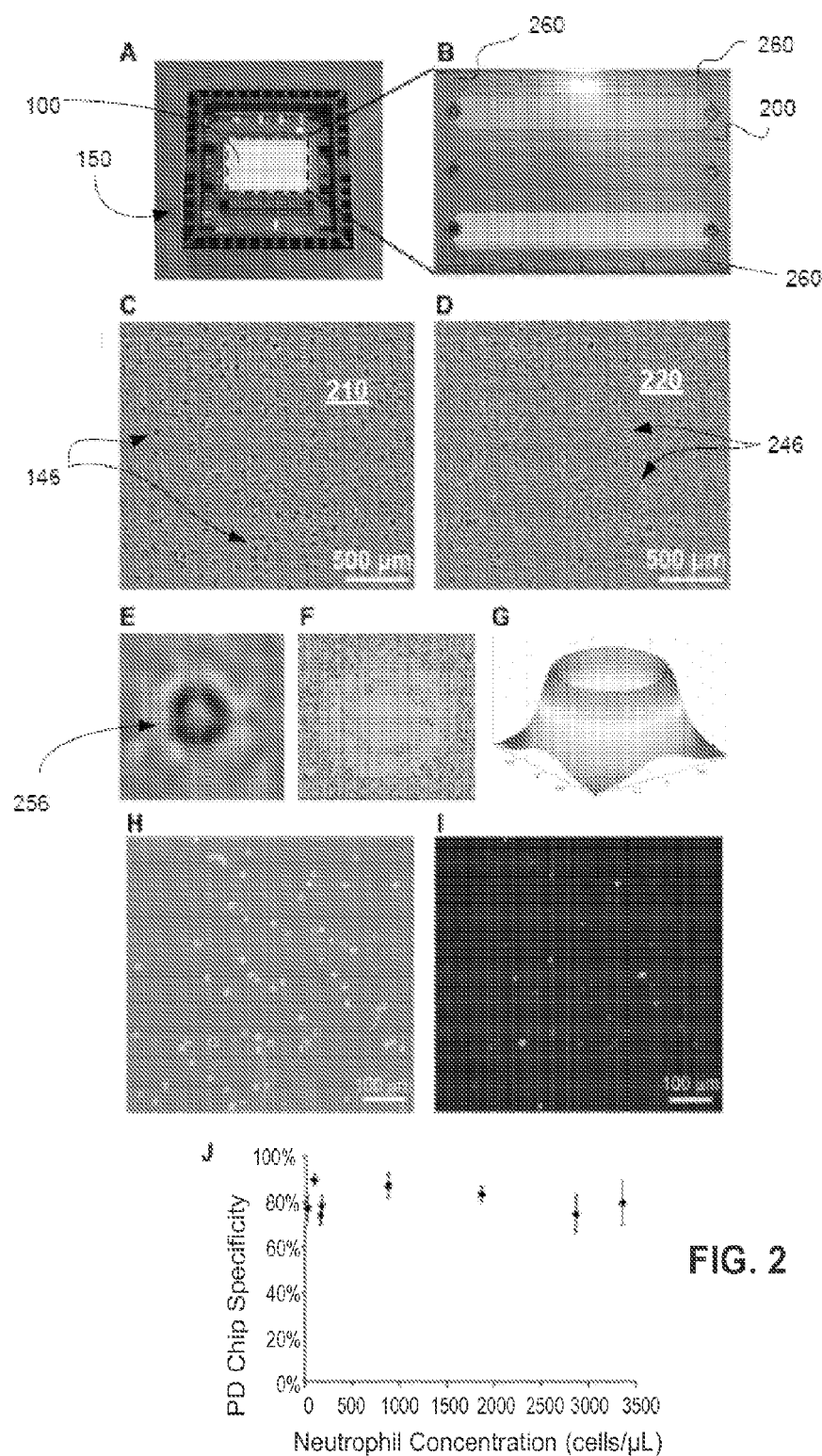
FIG. 2 presents images A through I illustrating operation of a computer program product and a method of the invention. The diagram J shows a plot of neutrophil capture specificity with the use of an embodiment of the chip over a wide neutrophil concentration range.
Figure 3:
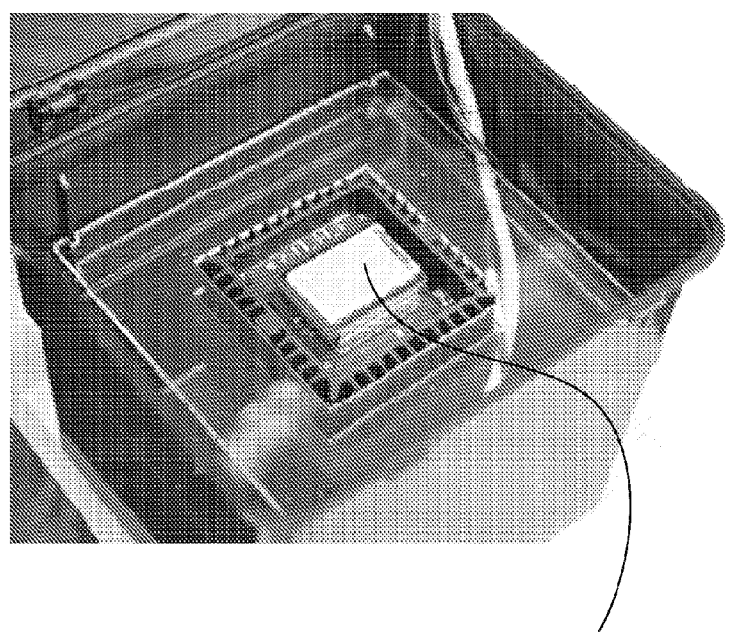
FIG. 3 shows, in perspective view, a detector and a chip adapted for imaging according to an embodiment of the invention.

The diagram A of FIG. 2 and FIG. 3 illustrate the positioning of the specific embodiment 100 on top of the CCD 150 without an optical component therebetween. The diagram B of FIG. 2 shows an image 200 of the embodiment 100 produced with the CCD 150. The diagram C of FIG. 2 provides a shadow image 210 of cells 146 captured on a surface of a channel 100a, which are later marked by an embodiment of the computer program product of the invention to produce the overall cell count. The marked with green color cells 246 are shown in the diagram D of FIG. 2. Following this procedure, images of individual cells are identified by modifying contrast of such images, an example of which is shown in an image of the cell 256 of the diagram E of FIG. 2. The diagrams illustrating noise reduction associated with the processing of imaging data and frequency domain transformation procedures, as well as data filtering with the use of a 3D passband filter are illustrated in the diagrams F and G of FIG. 2, respectively.

Embodiments of the Algorithm

To complement an algorithm of the invention (referred to herein as the HVC method), an embodiment of the computer program product of the invention includes program code for processing image data, received by the electronic data-processing computer circuitry (which maybe referred to as a processor, for short) after an initial phase of image restoration, with the use of frequency domain (FD) operations. After the FD-processing, the data are re-processed using spatial domain (SD) operations to produce a final result based on an intersection of the two outputs. The computer program product may include program codes to effectuate the following steps:

i. Automatic and/or manual selection of channels on a chip
ii. Image restoration to improve image contrast
iii. Frequency domain band-pass filtering
iv. Round object detection using matched filtering
v. Fine tuning the matches found by (iii) and/or (iv), and
vi. Incorporating user feedback to update the threshold specifying which objects should be counted as cells.

The above-mentioned steps of an embodiment of the image-processing algorithm of the invention are described below.

Automatic and/or Manual Selection of Channels on a Chip.

It may be required to count the cells in each of the channels 100a of the chip 100 of FIG. 1 separately. In doing so, not all of the area within the borders of a channel should be considered due to optical "smearing" of images of the cells near the boundary of a channel, which is an imaging drawback unique to each CCD image. Embodiment of the invention addresses this problem by providing the user with the following options.

Fully Automatic Mode.

Figure 4:
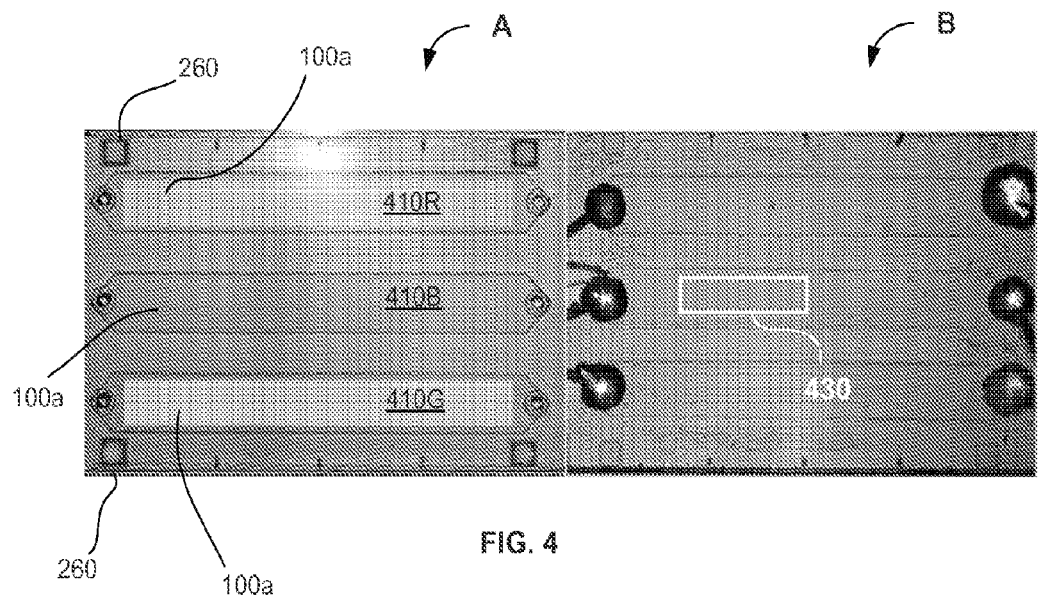
FIG. 4 includes images A and B of a PD microfluidic chip according to one embodiment.

This mode is built-in for the mass processing of images taken on a particular chip. In further reference to FIGS. 1 and 2, several pre-determined identifying markers (such as square markers 260 in the image of the diagram of FIG. 2, for example) can be engraved/imprinted on each corner of the chip 100 for localization and orientation of the channels 100a using the morphological data processing algorithm (such as, for example, the hit-miss transform in Matlab's image processing toolbox), with a structural element equal to the binary mask of the marker. For each chip carrying such markers, the user is enabled to generate a 'template' identifying the markers 260 (squares as shown) and the areas inside the channels 100a in which the count should be performed. FIG. 4 shows images A and B with the insides of the four squares 260 marked with a magenta asterisk. The areas inside the three channels 100a (of the image A), where the cell counting should be performed are highlighted with red (410R), green (410G) and blue (410B). Small variations in the placement of the chip 100 under the CCD 150 (such as a degree of parallelism between the chip and the surface of the CCD, for example) can be tolerated. For chips without the identifying markers, this option works as long as the chip is placed under the CCD in a fashion consistent with the template. Once the computer system identifies or recognizes the presence and location/orientation of the channels of the chip, the morphological data processing algorithm automatically performs the cell count without waiting for further user input.

Semi-Automatic Mode.

In this mode, and in reference to image A of FIG. 4, the user generates one 'template' per chip, and the channels in each new image are automatically colored (for example, as discussed above, highlighted with red, green and blue shades). The program code idles and waits for the user input representing that the identification, fine-tuning of the borders of the channels and the channel selection is complete.

Fully Manual Mode.

In this mode, the computer program product enables the processor to allow the user to re-sizably and movably mark any region in an image (whether rectangular or square in shape, such as the area 430 of image B of FIG. 4, for example) which may be smaller than the length of a channel, and then to perform the cell count only in the marked isolated area 430.

Image Restoration.

If an acquired image has low contrast, a normalization and/or standardization procedure is performed to ensure that an image of a cell stands out against the background. In reference to an image 510 of FIG. 5A, for example, some of the acquired images include color images. It is appreciated that the color information does not add practical value to or modify the cell-counting task. The first step in one specific implementation of the image restoration procedure, according to an embodiment of the invention, is to convert the image 510 to a gray scale image 512. The gray scale image 512 may still be characterized by low contrast; in this case, the image histogram is stretched out (for example, with the use of Matlab's adapthisteq function), as shown at 514. Following this, using high-boost filtering, the high-frequency components in the image are enhanced, while the low-frequency components are maintained, at 516, to form a high-frequency-boosted image 518. This image is the input image to frequency domain filtering.

Frequency Domain Band-Pass Filtering.

Figure 5A:
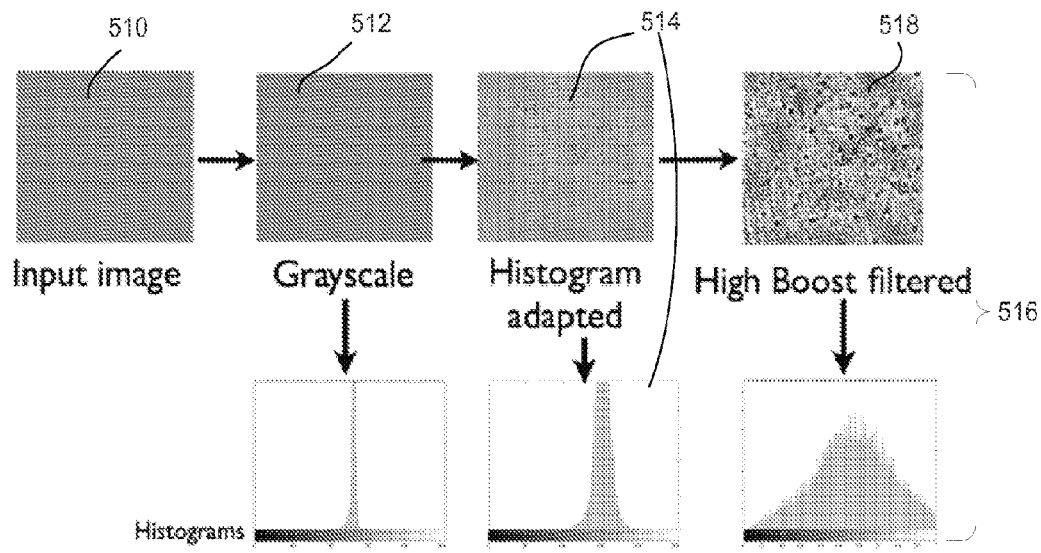
FIG. 5A is a diagram illustrating an embodiment of the image-restoration algorithm of the invention.
Figure 5B:
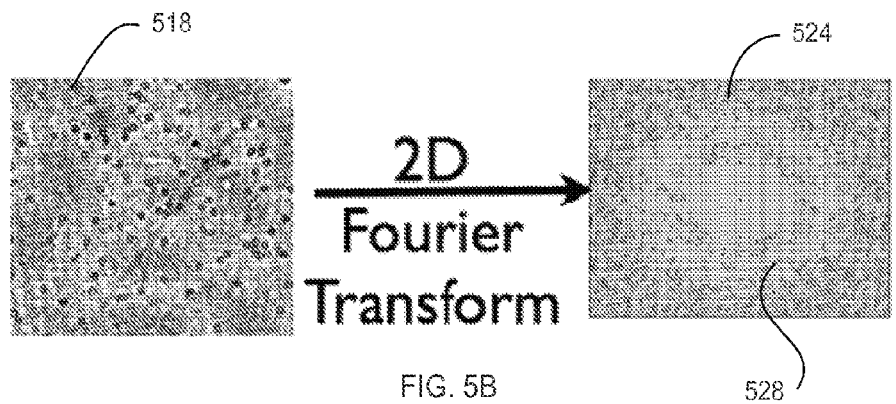
FIG. 5B is a diagram illustrating the transformation of a high-frequency-boosted filtered image to a frequency domain.
Figure 5C:
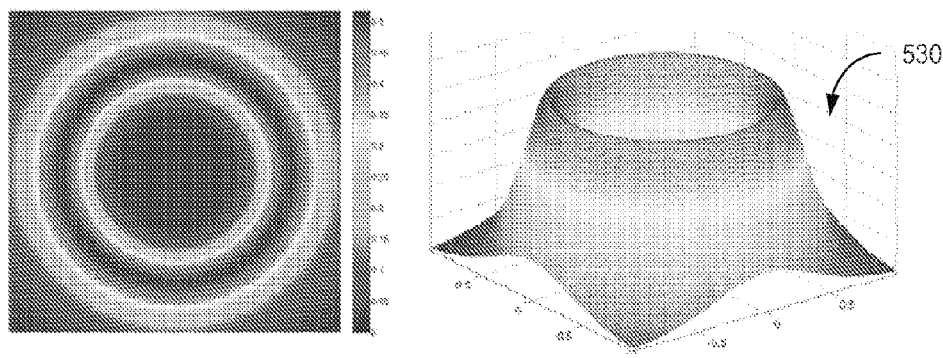
FIG. 5C provides a contour plot and a surface plot describing filtering characteristics of a band-pass filter used with an embodiment of FIG. 5A.

As a result of the boosting of high-frequency characteristics of the image 514, the 2D Fourier Transform 524 of the high-frequency-boosted filtered image 518 may exhibit a "halo" 528 shown in FIG. 5B. The halo 528 can be seen surrounding the high-energy area at low frequencies (at center of the frequency-domain image). The presence of this halo is due to the presence and nature of cells. Program code applying a custom-designed band-pass filter 530 to the Fourier Transform 524 of the image 518 reverts the transform 524 back to the spatial domain (not shown) and produces the effect of visually emphasizing the cells in the spatial image by removing spatial frequency components that do not contribute to the halo. Frequency characteristic of an embodiment of this custom filter are shown, in top and perspective views, in FIG. 5C.

While the frequency domain band-pass filtering emphasizes the cells and attenuates other unwanted elements of the image, cells are not the only contributors to the "halo" and some amount of noise remains. The noise-producing elements can include, for example, air-bubbles, fibers, and fine structures from the sample that are not cells. Instead of trying to handle each contribution to image noise, an embodiment of the HCC method of the invention takes advantage of the facts that (i) the cells of interest are almost always roundish and have substantially the same diameter; (ii) the imaging is carried out with the same system; (iii) the chip is always positioned at the substantially the same distance from the CCD. This makes it possible to use morphology of the cells of interest and identify round objects of a certain diameter, as discussed further below.

Detection of Round Objects Using Matched Filtering.

Figure 6:
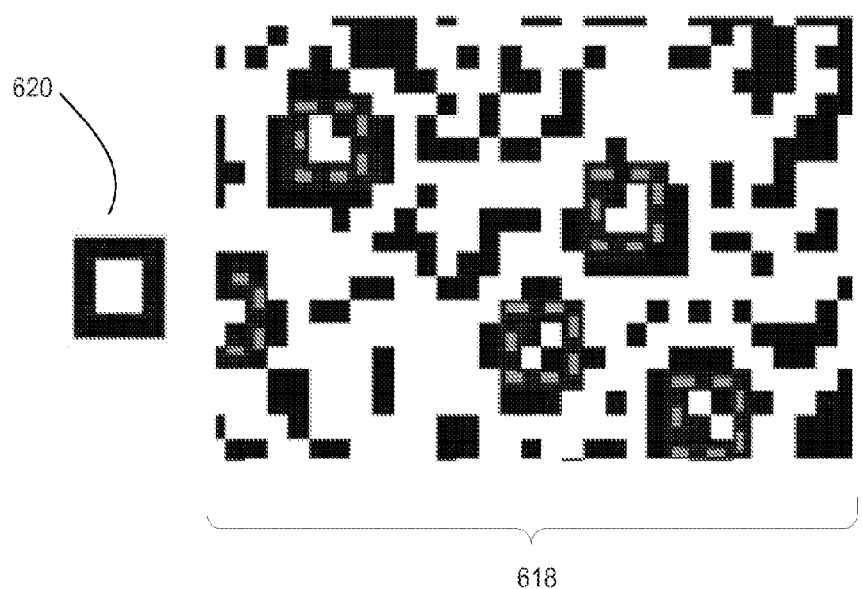
FIG. 6 provides binary versions of an image of a disk (on the left) and of a high-frequency boosted image of circular cells used with the process of the embodiment of FIG. 5A.

At this stage, the imaging data representing the high-boost filtered image 518 are used as input again. The image 518 is first converted into a binary image and then convolved with a template of a "disk". FIG. 6 illustrates a binary version 618 of the image 518 of FIG. 5, as well as the template 620 as a binary version of a roundish cell (the square shape satisfactorily approximates a disk in a noisy image) with which program code of the embodiment of the computer program product thereafter convolves the image 618.

Fine Tuning the Matches.

Figures 7A, 7B:
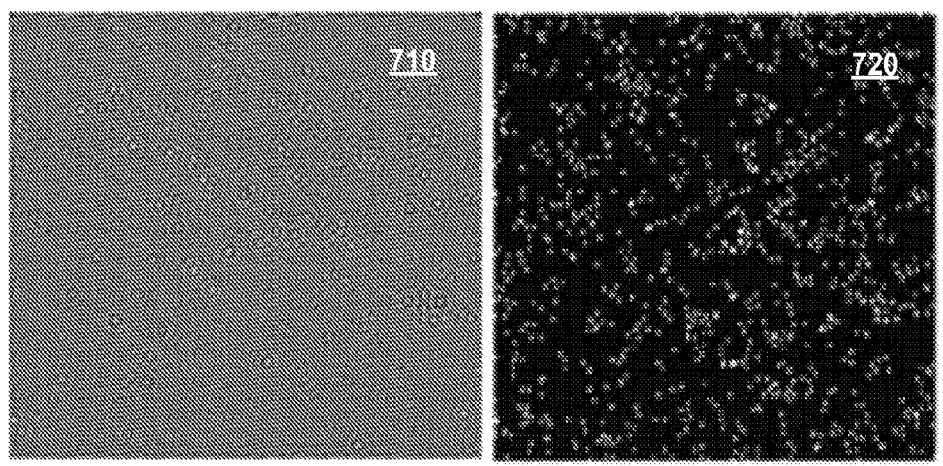
FIGS. 7A and 7B are, respectively, a gray scale image and a black-and-white image representing outputs of the frequency-domain filtering the spatial-domain filtering, according to an embodiment of the invention.
Figure 8:
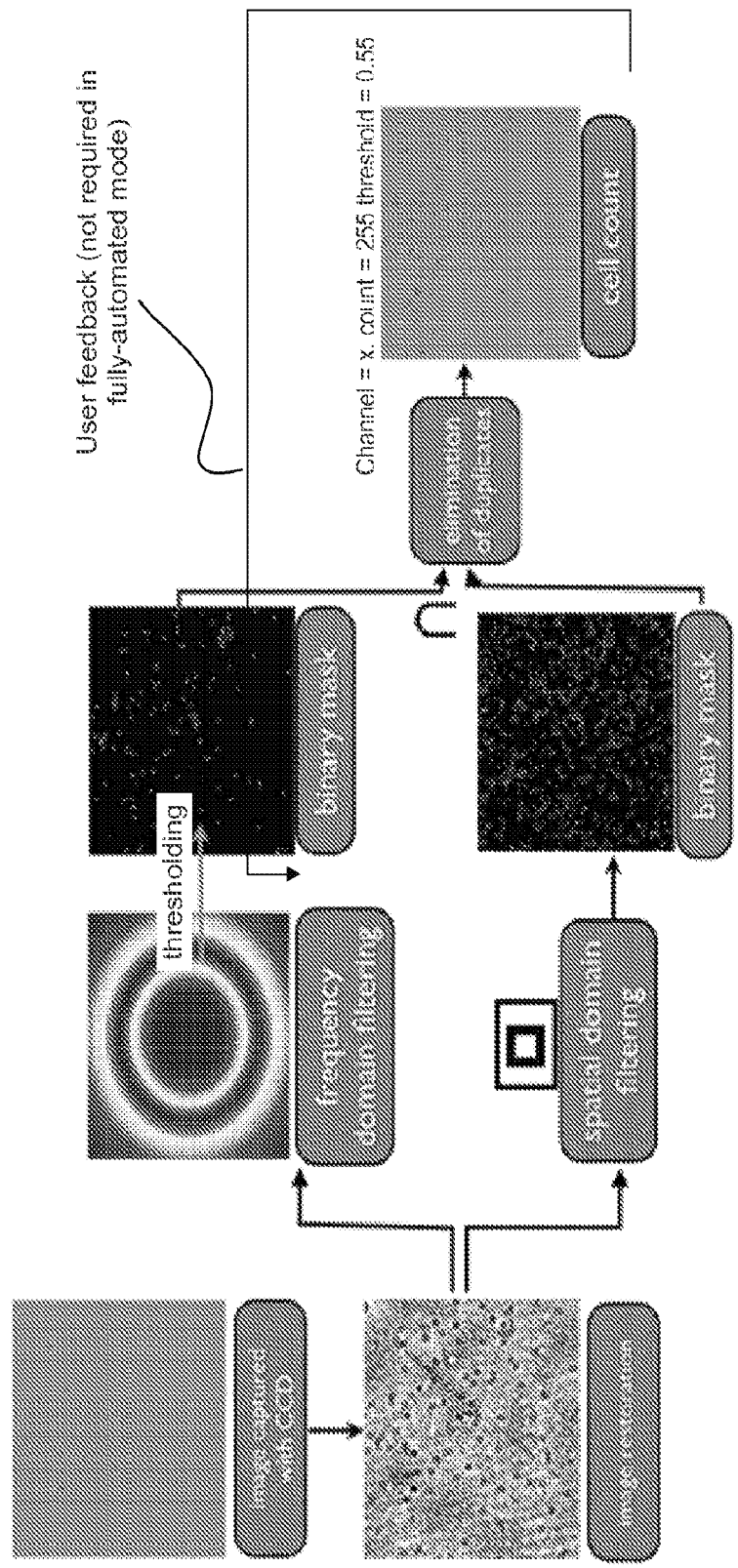
FIG. 8 is a flow-chart illustrating an embodiment of the image data processing algorithm.

FIGS. 7A and 7B show a gray scale image 710 and a black-and-white image 720 representing outputs of the frequency-domain filtering the spatial-domain filtering. The final count of cells is computed by finding the intersection of the results of thresholded black and white image 720 from frequency domain filtering and black and white image output from the matched filtering. In this binary intersection image, hits within three pixels of each other are collapsed into one. This is to ensure there are no duplicates and the cell count is not over-estimated.

Incorporating User Feedback to Update the Threshold Specifying which Objects should be Counted as Cells.

The final result depends on the value of the threshold that was specified. Once the counting of cells is accomplished, each valid cell is marked on the original image and displayed to the user for visual confirmation. At this point, the user has the ability to adjust the value of the threshold and, therefore, the results. The number of cells is displayed on the figure window and is dynamically updated. The higher the threshold, the fewer the number of points identified as cells but these have higher likelihood of actually being cells. The lower the threshold, more points are identified as cells but it the number of false positives generally increase.

The overall image processing algorithm described above is summarized in the flowchart of FIG. 8.

In the following portion of the disclosure, in reference to FIG. 9 and in further reference to FIG. 1, embodiments related to the structure of microchannels of the proposed chip to optimize the cell-capture (such as, for example, CD66b+ cells) are discussed in more detail. The flow dynamics and migration of $CD66b^+$ neutrophils to the microchip surface are characterized by multibody interactions of white blood cells ($CD66b^+$ neutrophils) and platelets, as illustrated in the diagram A of FIG. 9. At low shear rates, the increasingly blunted velocity profiles and enhanced $CD66b^+$ neutrophil margination have been observed in microvessels. For the purposes of this disclosure, the microchannels 100a with rectangular cross-sections were produced with two different heights (or depths), h=50 and 80 μm. Since the volume flow rates were set equal for both cases to Q=2 μl/min, the corresponding Reynolds numbers, $Re=\rho u h/\mu = \rho Q/\mu w$, are equal for both cases and equal to $Re \cong 0.01$. Here, ρ is the density of the fluid, Q is the volume flow rate, μ is the viscosity of the fluid, and w is the width of the channel. It is observed that the Reynolds number for the microchannels 100a is low, and the inertial forces are small compared to the viscous forces, and thus the flow may be characterized as a creeping flow for which Re<<1. The creeping flow on its own cannot resolve the underlying mechanisms for migration of neutrophils to the periphery of microchannels due to the well-known time reversibility of low Re flows. Time reversibility does not foster stiff $CD66b^+$ neutrophils to marginate to the microchip wall. Small curvature changes on the surface of $CD66b^+$ neutrophils can in theory cause to anti-symmetries, and thus transport of these cells by crossing the streamlines. However, this would be expected to slowly bring the $CD66b^+$ neutrophils to the microchannel center, rather than towards the wall.

Figure 9:
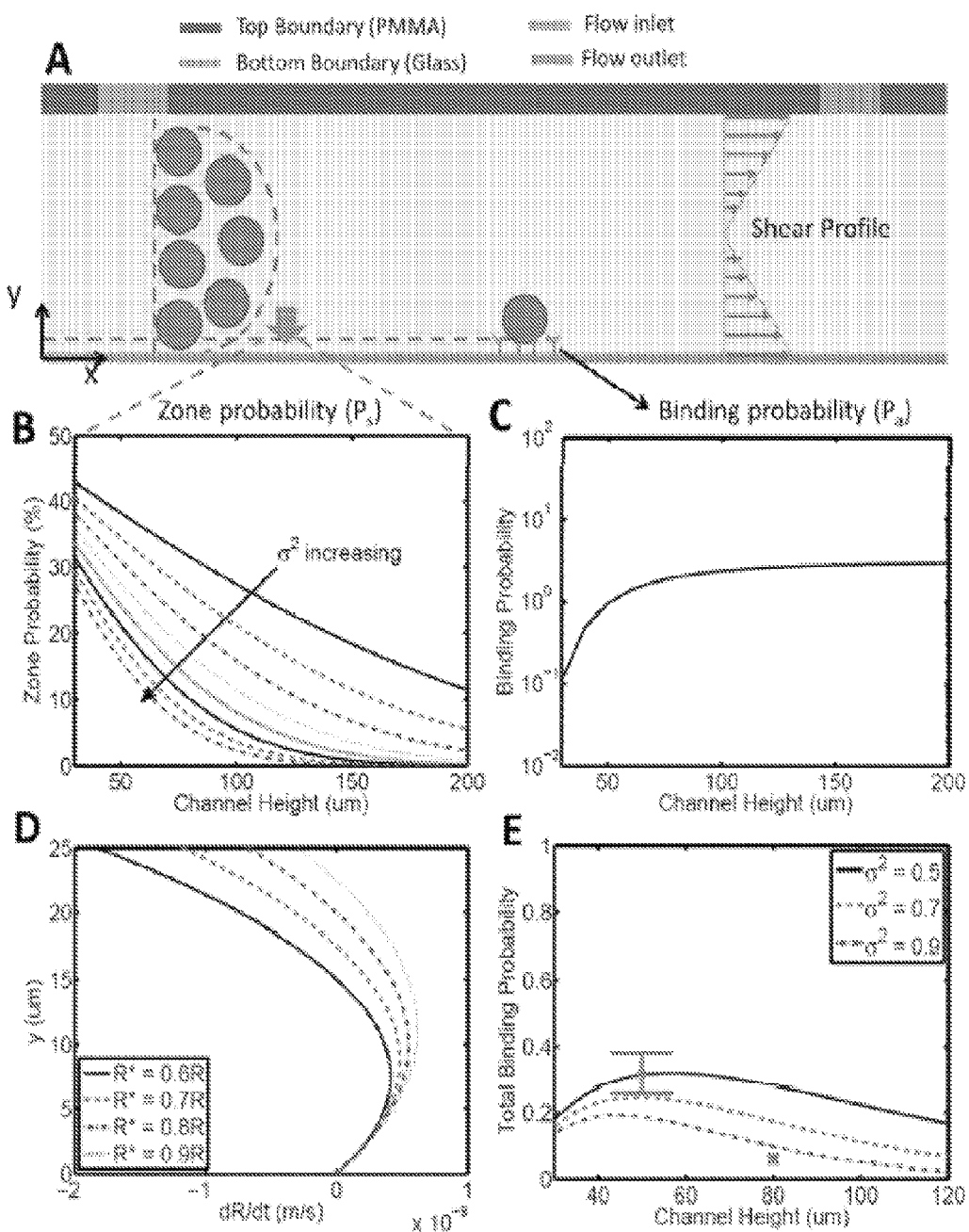
FIG. 9 present diagrams A through E illustrating the results of modeling of CD66b+ neutrophil capture according to an embodiment of the invention.

To design microchannels 100a of an embodiment 100 of FIG. 1 for effective capture of $CD66b^+$ neutrophils from patient dialysate samples, the present theoretical model, illustrated schematically in the diagrams B through E of FIG. 9, assumes that affinity-based cell-capture process includes two probabilistic periods.

These probabilities include (1) the probability that the cells in questions are located near the surface of the microchannel 100a and margination (if any) of cells towards equilibrium zones, which can potentially feed the cell population near the channel surface, as shown in the graph of the diagram B; and (2) the likelihood of bond formation between the cells locates near the channel surface and the receptors, as shown in the graph of the diagram C of FIG. 9. To determine the latter, the probabilistic kinetic formulation can be used. To assess the importance of margination, i.e. the migration of $CD66b^+$ neutrophils towards equilibrium zones, we first calculate margination velocities (shown in the graph of the diagram D of FIG. 9):

$$\frac{dy_{WBC}}{dt} = 0.17 \bar{u}^2 \frac{h\rho_0}{\varepsilon_0} \left(\frac{2a}{h}\right)^{2.84} \frac{2y_{WBC}}{h}\left(1 - \frac{y_{WBC}}{y^*_{WBC}}\right) \quad (1)$$

where $y_{WBC}$ is the vertical distance of $CD66b^+$ neutrophils, $dy_{WBC}/dt$ is the margination velocity, $y_{WBC}^*$ is the equilibrium vertical distance, a is the radius of $CD66b^+$ neutrophils, $\rho_0$ and $\epsilon_0$ are fluid density and viscosity. At the next step, the average margination velocity and average flow velocities are calculated as $u_m = [\int_0^h (dy_{WBC}/dt)dy]/h$, and $u_f = [\int_0^h u(y)dy]/h$, respectively. Following this calculating, time scales are compared by $t^* = (h/u_m)/(L/u_f)$.

As time scale ratio of margination and flow is >>1 ($t^* \sim 100$), initial distribution of neutrophils will be the determining factor. Here, we simply assume that cells will be normally distributed across the flow as:

$$P \cong \frac{1}{\sigma\sqrt{2\pi}} \exp\left(-\frac{(y-u)^2}{2\sigma^2}\right) \quad (2)$$

where μ is the mean location and $\sigma^{-2}$ is the variance of cell distribution. In further reference to the diagram B of FIG. 9, the probability for cells to be located in a thin zone between the channel surface and a threshold, $h_0$, (maximum distance) at which ligand-receptor bonds can be formed:

$$P_s \cong \frac{1}{\sigma\sqrt{2\pi}} \int_{\frac{h}{2}-a-h_0}^{\infty} \exp\left(-\frac{(y-u)^2}{2\sigma^2}\right) dy \quad (3)$$

The neutrophils were adhered to the bottom surface of the microchannel. The effective fluidic forces that can potentially dislodge neutrophils are given by $F=6\pi a l\mu S F^s$ and $M=6\pi a^3 \mu S T^s$ where l is the separation distance to the wall, μS is the shear stress at the wall, $F^s$ and $T^s$ are shape-dependent coefficients. The shear stress on microchannel surface, $\tau_w$, can be calculated as:

$$\Sigma_w = 6\mu Q/(wh^2) \quad (4)$$

Here, shear stresses are 0.0078 Pa for h=80 μm and 0.02 Pa for h=50 μm. Accordingly, and in further reference to the diagram C of FIG. 9, the steady-state adhesion probability is approximated as $$P_a = \pi r_0^2 \exp\left\{-\frac{\lambda}{k_b T}\left[6(a\gamma^{-1} + \delta_{eq})F^s + 8\frac{a^2}{r_0}T^s\right] \times \frac{a}{r_0^2}\frac{s}{m_r}\right\}(m_r m_l K_a^0) \quad (5)$$

where $m_r$ and $m_l$ are the receptor and ligand densities, respectively; $K_a^0$ is the association constant at zero load of the ligand-receptor pair; $A_c$ is the contact area; $\lambda$ is the characteristic length of the ligand-receptor bonds; $k_b$ is the Boltzmann constant; $F_{dis}$ is the dislodging force acting per unit ligand-receptor pair; $\gamma$ is the cell aspect ratio; and T is the temperature.

Finally, and in reference to the diagram E of FIG. 9, the combined probability of neutrophils captured by the surface is assessed as $P_t = P_s P_a$. The increase in total cell counts for both flow rates as neutrophil concentration increases can be easily attributed to the enhanced diffusion and collision dynamics of these cells towards the microchannel wall. For the same neutrophil concentration, a decrease in thickness of the microchannel leads to higher shear rates and an increase in total number of captured cells. Either packing larger number of cells in the same domain, or decreasing the size of the domain while keeping the number of cells constant leads to enhanced margination and increase in capture of neutrophils. Lastly, higher shear rates lead to larger detaching forces for the captured neutrophils, as well as longer exposure time for freely flowing neutrophils. If the process was dominated by the former phenomenon or its effect was amplified, it would cause to (faster) detachment of neutrophils and lower cell count.

Examples of Embodiments of Microfluidic Chip

Referring again to FIG. 1, in one implementation, the embodiment 100 was manufactured with the use of Poly (methyl methacrylate) (PMMA) (by McMaster Carr, Atlanta, Ga.) as the backing of the chip attached to an approximately 50 µm to 80 µm thick double-sided adhesive film (iTapstore, Scotch Plains, N.J.) to provide the channel height. Both components were cut to about 24×40 mm. Six pores of equal width were cut into the PMMA, with three pores at one end representing the inlets and the three pores at the opposite end representing the outlets. The channels, each 4.3 mm×25 mm long, were cut into the DSA; during, assembly these channels were aligned with each set of inlet and outlet pores and fixed onto the PMMA surface. Once the plasma-treated glass slide is centered and fixed on the remaining side of the DSA, the microfluidic chip is formed and ready for silanization. A length of a channel 100a was chosen to be about 30 mm as such length provided sufficient CD66b interaction for neutrophil immobilization. A channel width of about 4 mm provides an adequate amount of surface area for cell capture of approximately 100 µL PD sample. Glass slides (Corning, Lowell, Mass.) were plasma treated with oxygen plasma (at about 100 mW and 1% oxygen) for about 1 minute in the PX-250 chamber (March Instruments, Concord, Mass.) and used as a cap for the chip 100 to provide a tight seal to the channels 100a.

Examples of Functionalization of Microfluidic Channels

Materials for Channel Functionalization 200 proofs of ethanol (EtOH), for dilutions and washing of channels, and dimethyl sulfoxide (DMSO), the solvent for GMBS stock solution, were purchased from Sigma-Aldrich Chemical Company (St. Louis, Mo.). 3-mercaptopropyl trimethoxysilane (3-MPS), a silanization agent, was also purchased from Sigma-Aldrich Chemical Company (St. Louis, Mo.). N-y-maleimidobutyryloxy succinimide ester (GMBS), a coupling agent, was purchased from Pierce Biotechnology (Rockford, Ill.). 1× phosphate buffered saline (PBS) solution, for dilution of aqueous reagents and washing, was purchased from Gibco (Grand Island, N.Y.). NeutrAvidin, a functional protein for biotin binding, was purchased from Fisher Scientific (Fair Lawn, N.J.). Lyophilized albumin from bovine serum (BSA), for blocking nonspecific bindings/interactions, was purchased from Sigma-Aldrich Chemical Company (St Louis, Mo.). Biotinylated anti-human carcinoembryonic antigen-related cell adhesion molecule 8 (CEACAM-8) antibody, used for the capture of neutrophils in clinical PD samples, was purchased from R&D Systems (Minneapolis, Minn.).

Materials for Neutrophil Capture and Analysis.

The syringe pump, used for passing the PD sample through the microfluidic chip, was purchased from SyringePump.com (Farmingdale, N.Y.). The 1 mL Luer Lock syringes, used to inject the PD fluid through the microfluidic chip, were purchased from BD Biosciences (Franklin Lakes, N.J.). The 0.01" inner diameter nylon tubing, used to connect the syringes to the microfluidic chip, was purchased from Cole-Parmer (Vernon Hills, Ill.). The microfluidic chip was cleaned with Zeiss Lens Cleaner, purchased from Carl Zeiss Optical Inc. (Cleveland, Ohio). The charge-couples device (CCD), used for imaging of the chip to quantify neutrophil capture, was purchased from Imperx Inc. (Boca Raton, Fla.) and incorporated into the 'black box' with an LED light source with 86.9 kΩ resistance and 2.3V power source.

Solution Preparation.

Once the microfluidic chip was assembled, the procedure required to functionalize the microfluidic channels was performed, as outlined in Tables 2 and 3.

First, silanization solution was pipetted through each channel and incubated for 30 minutes. The silanization solution is a dilution of 200 mM 3-MPS in EtOH. GMBS Solution is a dilution of 2 mM GMBS solution in EtOH. NeutrAvidin solution is a 100 µg/mL solution of NeutrAvidin in PBS. 1% BSA solution is 10 mg/mL solution of BSA in PBS. Antibody solution is a 200 ng/mL solution of CEACAM-8 antibody in PBS (1000× dilution from stock).

Any unbound 3-MPS was flushed from the channel with EtOH. Next, GMBS solution was pipetted through each channel and incubated for 30 minutes. Unreacted GMBS was flushed from the channel with EtOH. The channels were then washed with PBS to remove the organic solvent. The NeutrAvidin solution was pipetted through each channel and incubated in darkness (due to light sensitivity) for 60 minutes for immobilization onto GMBS. Unbound NeutrAvidin was washed from the channel with PBS. Next, 1% BSA Solution was pipetted through each channel and incubated for 30 minutes for surface passivation. Unbound BSA was washed from the channels with PBS. Antibody solution was then pipetted through each channel, incubated for 30 minutes, pipetted through each channel again, and incubated for 30 more minutes.

TABLE 2

An Example of Operating Procedure for microfluidic chip fabrication and
initial functionalization (all steps are carried out at Room Temperature)

| Step | Description | Requirements | Duration | Specifications |
|---|---|---|---|---|
| 0 | Glass Slide Cleaning | Wipe with Ethanol | ~20 s per side | Dry with $N_2$ gas |
| 1 | Glass Slide Plasma Treatment | Air Plasma | 90 s | — |
| 2 | Assembly | Glass Slide and PMMA connected with DSA | — | Ensure plasma treated face of slide is inside channels |
| 3 | 3-MPS Treatment | 100 μL pipetted through each channel | 30 min incubation | Silanization solution in EtOH used. Wrap pores in parafilm to prevent evaporation |
| 4 | Ethanol Rinse | 100 μL pipetted through each channel | — | 200 proofs EtOH is used |
| 5 | GMBS treatment | 100 μL pipetted through each channel | 30 min incubation | GMBS Solution in EtOH used. Wrap pores in Parafilm to prevent evaporation |
| 6 | Ethanol Rinse | 100 μL pipetted through each channel | — | 200 proofs EtOH is used |
| 7 | PBS Rinse | 300 μL pipetted through each channel | — | Filtered PBS is used. |
| 8 | NeutrAvidin treatment | 15 μL pipetted through each channel | 60 min incubation | NeutrAvidin solution in PBS used. Wrap pores in parafilm to prevent evaporation. |
| 9 | PBS Rinse | 100 μL pipetted through each channel | — | Filtered PBS is used. |
| 10 | BSA application | 15 μL pipetted through each channel | 30 min incubation | 1% BSA solution in PBS used. Wrap pores with parafilm to prevent evaporation. |
| 11 | PBS Rinse | 30 μL pipetted through each channel | — | Filtered PBS is used. |
| 12 | Storage | Do not proceed to Table S2 until PD sample is obtained | — | Chip is in chemically stable state. |

PBS: Phosphate Buffered Saline
EtOH: 100% Ethanol

TABLE 3

An Example of Operating Procedure for application
of surface chemistry within microfluidic channels.

| Step | Description | Requirements | Duration | Specifications |
|---|---|---|---|---|
| 0 | Initiate Application of Surface Chemistry | This process requires approximately one hour to complete. For optimal results, the clinical sample should be ready immediately following second antibody incubation. | | |
| 1 | Antibody application | 15 μL pipetted through each channel | 30 min incubation | Antibody solution in PBS is used. Wrap pores with parafilm to prevent evaporation. |
| 2 | PBS Wash | 30 μL pipetted through each channel | — | Filtered PBS is used. |
| 3 | Antibody application | 15 μL pipetted through each channel | 30 min incubation | Antibody solution in PBS is used. Wrap pores with parafilm to prevent evaporation. |

Examples of Capture of Neutrophils within
Microfluidic Channels

In reference to Table 4, the syringes and the syringe pump were set up. Each syringe was filled with 200 μL clinical PD sample (three syringes per sample). 30-gauge, Luer Lock, blunt needles were attached to the syringes; nylon tubing was fitted to the pointed end of each needle. The syringes were then loaded into the syringe pump. The pump was run until all of the plungers were at the same level and fluid was flowing the nylon tubing. Then, the free end of each piece of nylon tubing was epoxied into each respective inlet port in the microfluidic chip. A 200 μL pipette tip was placed in each outlet port for depleted sample collection. The syringe pump was run until 100 μL passed through each microfluidic channel. Then the tubing and pipette tips were removed from the microfluidic chip inlets, the surfaces of the microfluidic chip were cleaned using the Zeiss Lens Cleaner. Finally, the microfluidic chip was placed on the CCD image sensor, and an image was saved on the computer for quantification, as discussed above.

TABLE 4

An Example of Operating Procedure for testing clinical peritoneal
dialysis (PD) samples with functionalized surface chemistry.

| Step | Description | Requirements | Duration | Specifications |
|---|---|---|---|---|
| 0 | Preparations | Set up Syringe Pump to flow sample through chip | — | Fill three syringes per sample with >100 µL PD sample each; connect syringes to microfluidic chips; load syringe pump |
| 1 | PD Sample Injection | Syringe Pump is run | 50 min | 2 µL/minute, 100 µL sample passed through chip |
| 2 | PBS Wash | 100 µL pipetted through each channel | — | Filtered PBS is used |
| 3 | Surface Cleaning | Wipe the outsides of the microfluidic chips thoroughly | — | 70% EtOH is used |
| 4 | CCD Imaging | Clean image sensor; place microfluidic chip directly image sensor; save images to hard drive | — | Image sensor is cleaned directly with lens paper and lens cleaning solution |
| 5 | Automatic Cell Counting | Images are analyzed using the MATLAB function | — | Adjust parameters to ensure accurate counting numbers |
| 6 | Manual Cell Counting (if necessary) | Images are analyzed and a manual cell count is performed | 30 minutes | A manual cell counter, in conjunction with the magnified digital image, is used. |

Figure 10:
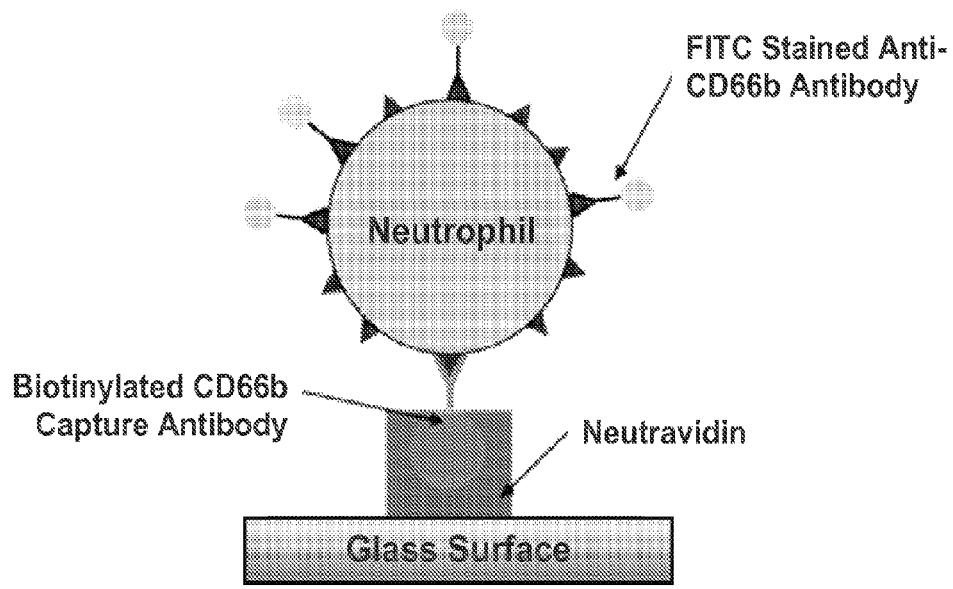
FIG. 10 is a schematic diagram showing bounding of a neutrophil cell to a surface of a chip while stained with FITC-CD66b antibody.

Demonstration of Robust Performance of an Embodiment of Microfluidic Chip in Analysis of Turbid PD Dialysate Samples The proposed embodiments of the PD microfluidic chip possess the ability to provide accurate results even while a sample procured from the PD patient samples contains additional particles such as fibers or RBCs. In particular, and in reference to FIG. 10, one implementation of the microchip includes an immunoassay based chip in which any bound neutrophils remain on the surface while other particles are removed by a wash buffer.

Figure 11:
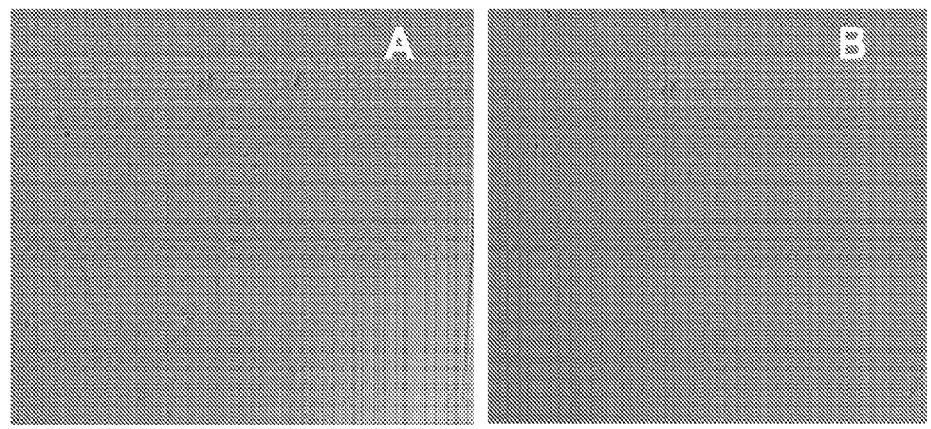
FIG. 11 shows images A and B representing, respectively, a channel of a chip following the injection of a turbid PD sample and the same channel following the PBS flushing procedure.

The effect of degree of opaqueness of a fluid sample on the quality of optical imaging was also addressed. It was determined that the PD fluid with high particle concentrations did not have an effect on the CCD image when following the flush with wash buffer. If the PD chip was imaged before samples were flushed however, the noise in the CCD image would be significant. As illustrated in FIGS. 11A and 11B, for example, a PD sample with high degree of opaqueness (turbidity) was injected in the embodiment 100 of the PD chip and imaged immediately after that to produce the image of FIG. 11A. The same sample was additionally imaged following the PBS flushing step to produce an image of FIG. 11B. The turbidity increase was a result of fibers accumulating in the PD dialysate. The comparison between the images of FIGS. 11A and 11B shows the significant decrease in noise that occurs when a wash buffer is added. Despite the high turbidity of the fluid, the CCD 150 was still capable of providing a clear image of the overall capture on the surface.

Figure 12:
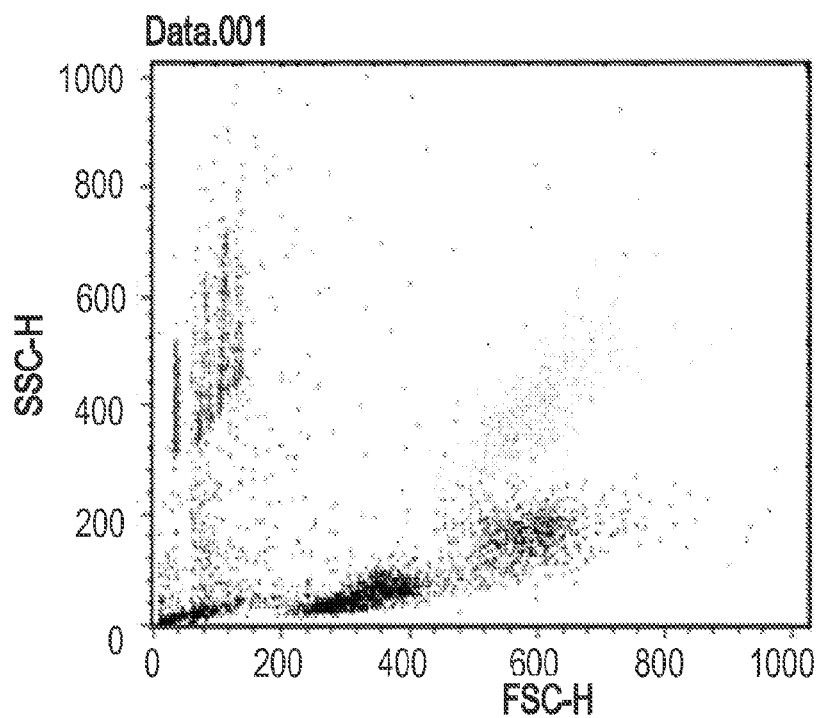
FIGS. 12A through 12F are FCS plots representing examples of analyses of PD samples.
Figure 12:
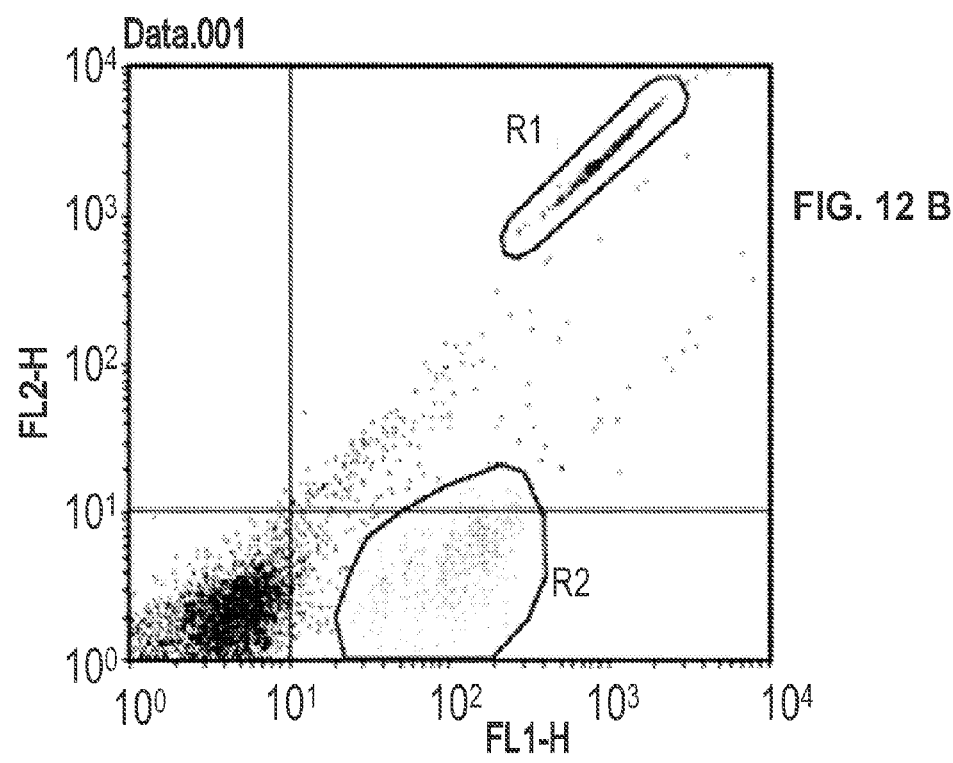
Figure 12:
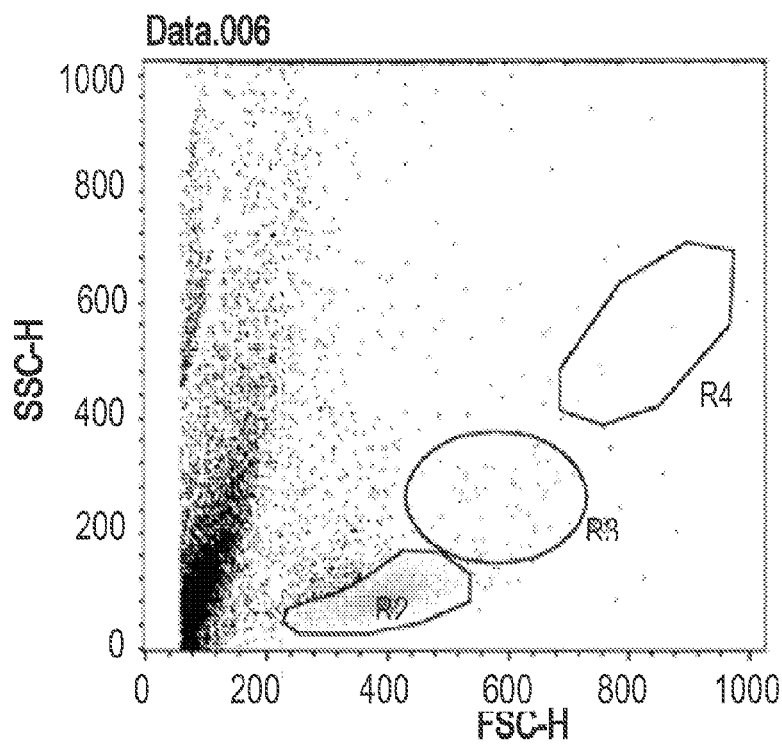
Figure 12:
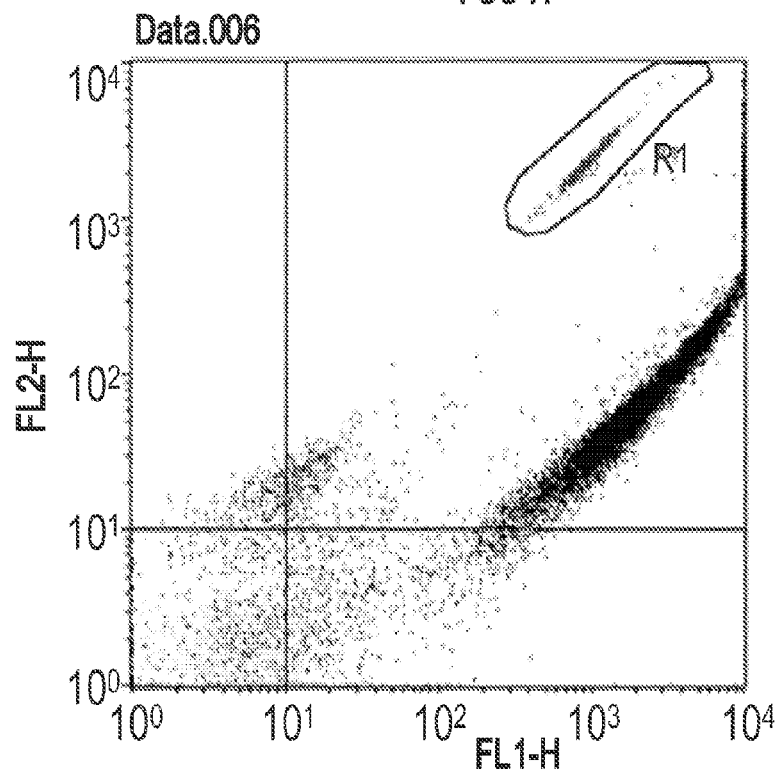
Figure 12:
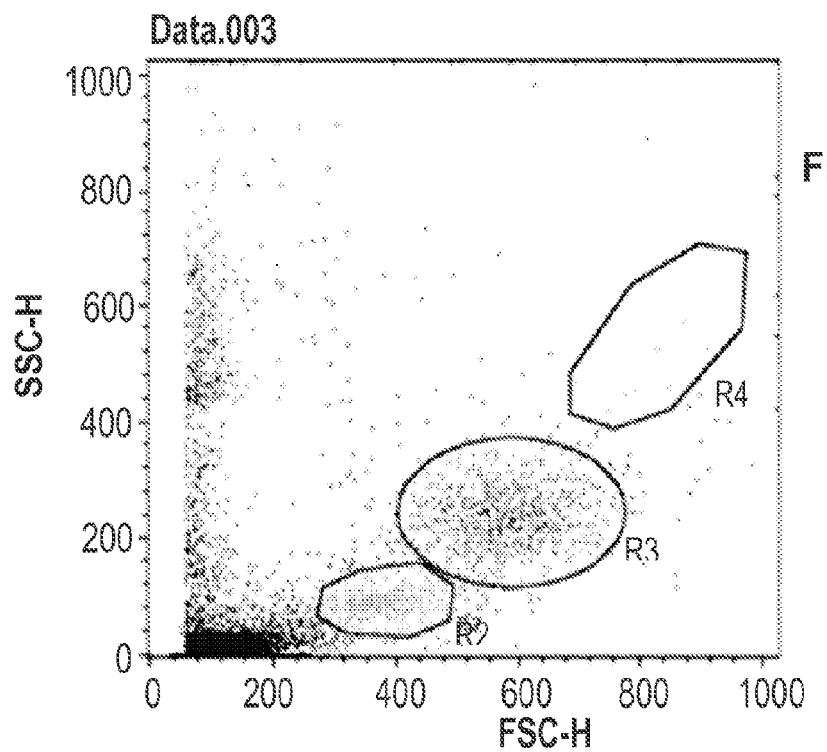
Figure 12:
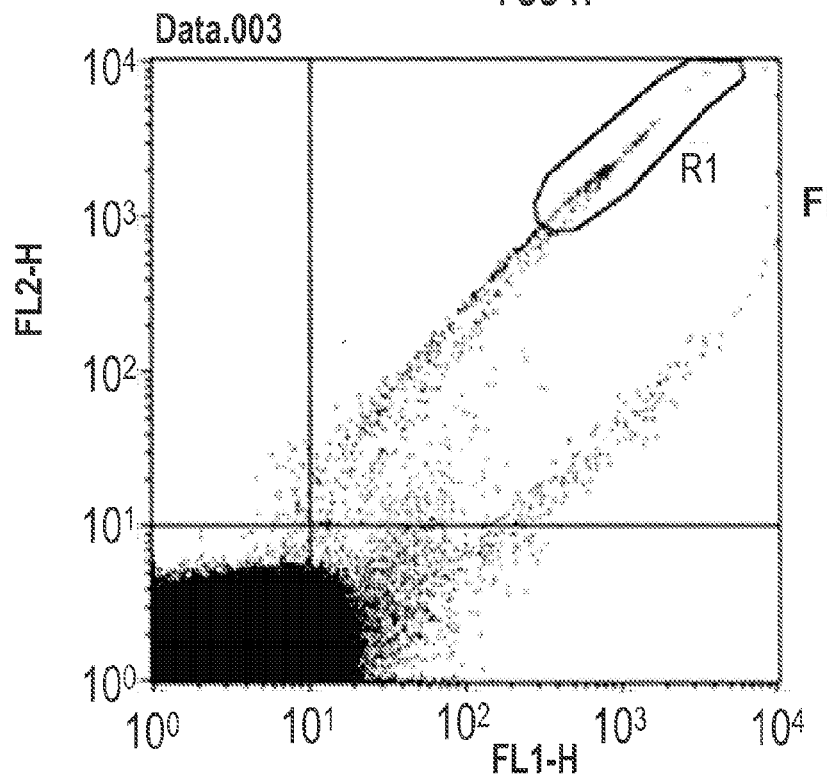

FACS results were also affected by various particles in the PD fluid. Dead cells often cause noise in the FACS images making it difficult to gate the target cells such as neutrophils. With the increase in the overall particle number there is also an increase in time needed for determination of cell concentration values. FIGS. 12A and 12B provide FACS plots characterizing a typical sample that includes lymphocytes, monocytes and neutrophils. The neutrophils stained with FITC-CD66b are gated and displayed in the corresponding FSC vs. SSC region. FIGS. 12C and 12D provide FACS plots representing results of the characterization of a turbid PD sample procured from the patient. Dead cells as well as additional particles cause noise levels to increase in FSC vs. SSC, thereby complicating the gating of the cells (as can be seen from a plot region to the left of the gated R2 region of FIG. 12C, for example). At such noise levels it becomes difficult to determine specific cell counts and accurately determine cell concentrations. FIGS. 12E and 12F show the FACS plots characterizing a sample obtained from a patient who uses Icodextrin as his dialysate sugar (as opposed to the traditional dextrose dialysate). Icodextrin, being a high molar mass sugar, is recognized on the flow cytometer as an event. As a result, more than 100× the events is required to obtain a considerable WBC concentration.

Figure 13:
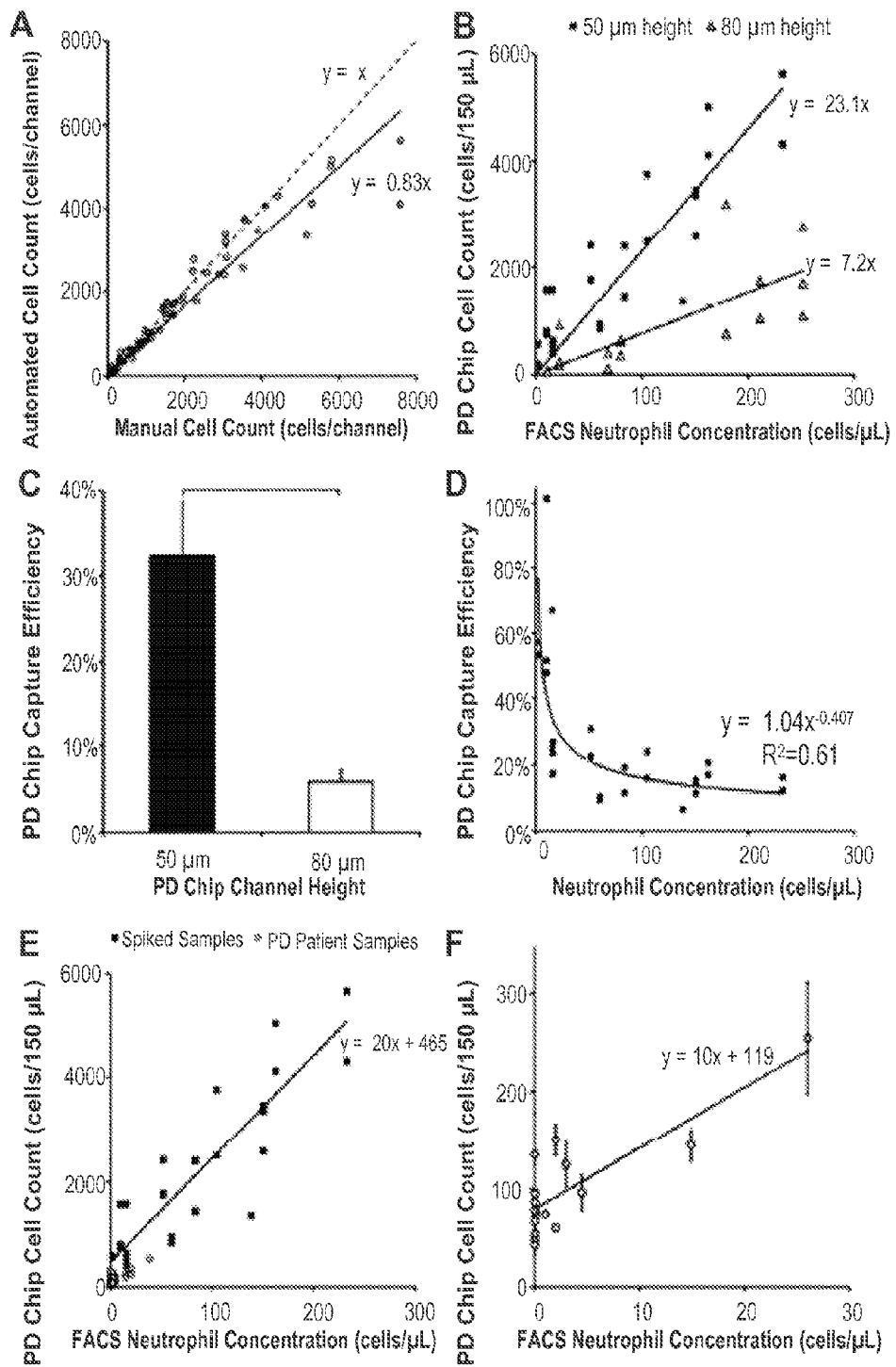
FIGS. 13A through 13F are plots showing the results of validation of operationability of an embodiment of the invention.

FIG. 13 shows plots A through F illustrating validation of operationability of embodiments of the invention. FIG. 13A is a plot demonstrating the results of statistical comparison of automated counting the neutrophils in the PD sample according to embodiments of the invention and manual cell counting. A high correlation ($r=0.96$, $p<0.01$) between manual and software cell counts was observed. FIG. 13B is a plot showing the effect of channel dimensions and flow rate on neutrophil capture efficiency and demonstrating higher capture efficiency attained with 50 µm channels as compared to 80 µm channels discussed above. Further, 50 µm high design provided a higher correlation ($r=0.90$, $p<0.01$) to flow cytometer neutrophil counts, compared to 80 µm high channel design ($r=0.74$, $p<0.01$). FIG. 13C is a plot representing neutrophil counts performed on PD patient samples. A significant correlation ($r=0.90$, $p<0.01$) between sample neutrophil concentration and PD chip cell count was observed. FIG. 13D is a plot representing dependence of capture efficiency of an embodiment of the PD chip as a function of neutrophil concentration in samples described in Table 2. The microchip counts with PD patient samples displayed statistically significant correlation ($r=0.83$, $p<0.05$) with FACS counts. Measurement of the clinical samples, the results of which are shown in FIGS. 13E and 13F, indicated significant correlation (Pearson correlation: 0.90, $p<0.01$) between the flow cytometry results (gold standard) and the microchip for neutrophil counts in the range of 0 to 300 cells/µL. Such range covers the clinically relevant detection range.

In accordance with examples of embodiments, a microfluidic system and a method for an early detection of infection and documenting of PD hygiene compliance rates are provided. A home healthcare portal for improved management of peritoneal dialysis therapy, discussed in this disclosure, is adapted to aid the clinician in monitoring healthcare of the patient at a point-of-care. The inventors are not aware of any POC rapid technologies existing to monitor PD fluid at the bedside of the patient. The envisioned embodiments utilize the discard PD fluid and to enable count of the WBC and neutrophils in the fluid. Based on such measurement of a PD, the system provides an indicator (such as a color indicator, red or green LED, for example) in response to which the communication between the clinician and the patient is initiated leading to a clinical decision regarding a potential infection, thereby reducing or eliminating a time-delay of treatment. The recorded data will be sent to an electronic record where patient, the caregivers can access. The diagnostic decision will be made still by the doctor and the nurse interacting with the patient. The proposed embodiments replace unreliable cloudiness or turbidity based measurement methodologies for the benefit of the patient avoiding acute cases, time delays and providing a more patient-friendly PD characterization method than hemodialysis.

While specific values chosen for these embodiments are recited, it is to be understood that, within the scope of the invention, the values of all of parameters may vary over wide ranges to suit different applications.

Implementation of a method of the invention and/or enablement of the operation of a system of the invention described above may be effectuated with a use of a processor specifically and particularly programmed to perform the steps of the required algorithm. Such processor can be controlled by instructions stored in a tangible, computer-readable memory. Those skilled in the art should readily appreciate that instructions or programs defining the functions of the present invention may be delivered to a processor in many forms, including, but not limited to, information permanently stored on non-writable storage media, information alterably stored on writable storage media, or information conveyed to a computer through communication media, including wired or wireless computer networks. In addition, while the invention may be embodied in software, the functions necessary to implement the invention may optionally or alternatively be embodied in part or in whole using appropriate firmware and/or hardware components (such as, for example, combinatorial logic, Application Specific Integrated Circuits, and Field-Programmable Gate Arrays).

While the invention is described through the above-described exemplary embodiments, it will be understood by those of ordinary skill in the art that modifications to, and variations of, the illustrated embodiments may be made without departing from the disclosed inventive concepts. Accordingly, the invention should not be viewed as being limited to the disclosed embodiment(s).

What is claimed is:

1. A system for at least one of identifying and counting target cells in a bodily fluid sample, the system comprising:
    an element with a network of microfluidic channels,
    an optical detector positioned adjacently to the element to acquire a shadow cast by the element onto the optical detector in light that has passed through the element wherein said system is devoid of an optical component between the element and the optical detector, and
    a non-transitory computer-readable medium having computer readable program code disposed therein, for at least one of identifying and counting the target cells in the bodily fluid sample, and comprising a series of computer-readable program steps to effect:
        acquiring data representing an initial image, of at least one channel from the network of microfluidic channels, formed on a surface of the optical detector by said shadow in said light that has traversed the at least one channel;
        converting the acquired data to data representing a gray-scale image of said at least one channel;
        data-processing of so-converted data by filtering these data in at least one of a frequency domain and a spatial domain; and
        when said at least one channel of said network of microfluidic channels contains the bodily fluid sample with identified biological cells, identifying and optionally counting target cells in relation to parameters of said at least one channel and a predefined threshold value.

2. The system according to claim 1, further comprising a display in operable communication with said computer readable medium, wherein computer readable program code further comprises a series of computer readable program steps to effect presenting said initial image at the display, said initial image containing visually perceivable marks representing said counted identified cells.

3. The system according to claim 1, wherein computer readable program code further comprises a series of computer readable program steps to effect submitting said count value to a server in communication with said computer readable medium.

4. The system according to claim 3, wherein computer readable program code further comprises a series of computer readable program steps to effect receiving, from a user of said server, an input representing a change to the predetermined threshold value and displaying, based on such input, at least one of a gray-scale image and a color image containing marks that identify the counted identified cells in relation to a changed threshold value.

5. The system according to claim 1, wherein said converting includes processing the acquired data to change a corresponding spectrum of spatial frequencies such as to increase amplitudes of high frequency components of the spectrum while maintaining amplitude of low frequency components of the spectrum.

6. An article of manufacture comprising
    data-processing circuitry and
    a computer readable medium comprising computer readable program code disposed therein for counting target cells in a bodily fluid sample contained in a channel of a microfluidic system, which system includes
        a microfluidic chip having one or more microfluidic channels;
        an optical detector adjacent to said microfluidic chip; and
        a light source configured to transmit light through said microfluidic chip onto the optical detector,
        wherein the system is configured to cast a shadow at the optical detector in said light in absence of an optical component defined to form an optical conjugate of said sample at the optical detector, said shadow having an irradiance distribution representing the bodily fluid sample at the optical detector;
    said computer readable program code comprising a series of computer readable program steps to enable at least one of identifying and counting of the target cells based at least in part on conversion of data representing the formed irradiance distribution to a gray scale.

7. The article of manufacture according to claim 6, wherein the computer readable program code further comprises steps to enable said counting based on a probability of the target cells to be located near a surface of a channel and a likelihood of bond formation between so located target cells and receptors.

8. A method for identifying cells contained in a bodily fluid sample, the method comprising:

receiving data representing an image of target cells in the bodily fluid sample formed in light that has traversed a microfluidic channel containing said bodily fluid sample and cast a shadow of said microfluidic channel on an optical detector, wherein the receiving data includes receiving data representing said image of said target cells produced without the use of an optical component configured to form an optical conjugate of said target cells at the optical detector; and processing the received data to determine a count of the neutrophils target cells in the bodily fluid sample based on probability of the neutrophils said target cells to be located near a surface of the microfluidic channel and a likelihood of a bond formation between so located neutrophils target cells and receptors.

9. The method according to claim 8, further comprising determining probability of a steady-state adhesion of the target cells to the surface of the microfluidic channel.

10. The method according to claim 8, further comprising generating visually-perceivable triggering indicator when the count exceeds a threshold value that is adjustable based on a user input.

11. The method according to claim 8, wherein said target cells include one or more of neutrophils, lymphocytes, and monocytes.

\* \* \* \* \*

UNITED STATES PATENT AND TRADEMARK OFFICE
CERTIFICATE OF CORRECTION

PATENT NO. : 9,518,914 B2  
APPLICATION NO. : 14/430360  
DATED : December 13, 2016  
INVENTOR(S) : Umut A. Gurkan et al.

Page 1 of 1

It is certified that error appears in the above-identified patent and that said Letters Patent is hereby corrected as shown below:

In the Specification

Column 12, Line 56 Equation 4 "$\Sigma_w = 6\mu Q/(wh^2)$" should be -- $\tau_w = 6\mu Q/(wh^2)$ --

Signed and Sealed this  
Sixteenth Day of May, 2017

Michelle K. Lee  
*Director of the United States Patent and Trademark Office*